United States Patent [19]

Tanaka

[11] 4,264,308
[45] Apr. 28, 1981

[54] DENTAL METHOD FOR FABRICATING RESTORATIONS

[76] Inventor: Asami Tanaka, 4840 Foster St., Skokie, Ill. 60077

[21] Appl. No.: 946,877

[22] Filed: Sep. 29, 1978

[51] Int. Cl.³ .......................... A61C 5/10; A61C 9/00
[52] U.S. Cl. ...................................... 433/223; 433/70; 433/50; 433/75
[58] Field of Search ................ 32/12, 19, 32, 8, 40 R; 264/19; 433/70, 215, 223, 50, 75

[56] References Cited

U.S. PATENT DOCUMENTS

| | | | |
|---|---|---|---|
| 2,376,384 | 5/1945 | Ringle et al. | 32/32 |
| 2,539,773 | 1/1951 | Fournet | 32/8 |
| 2,752,681 | 7/1956 | Jankelson | 32/19 |
| 3,059,336 | 10/1962 | Windish | 433/70 |
| 3,068,571 | 12/1962 | Thompson | 32/40 R |
| 3,354,548 | 11/1967 | Segal | 32/32 |
| 3,918,160 | 11/1975 | Friedman | 32/19 |

*Primary Examiner*—Gene Mancene
*Assistant Examiner*—John J. Wilson
*Attorney, Agent, or Firm*—Neuman, Williams, Anderson & Olson

[57] ABSTRACT

This invention relates generally to a method and instrument for fabricating a first dental restorative having a predetermined standard occlusal contact relationship with an opposing second dental restorative and for fabricating a pattern for such first restorative.

5 Claims, 4 Drawing Figures

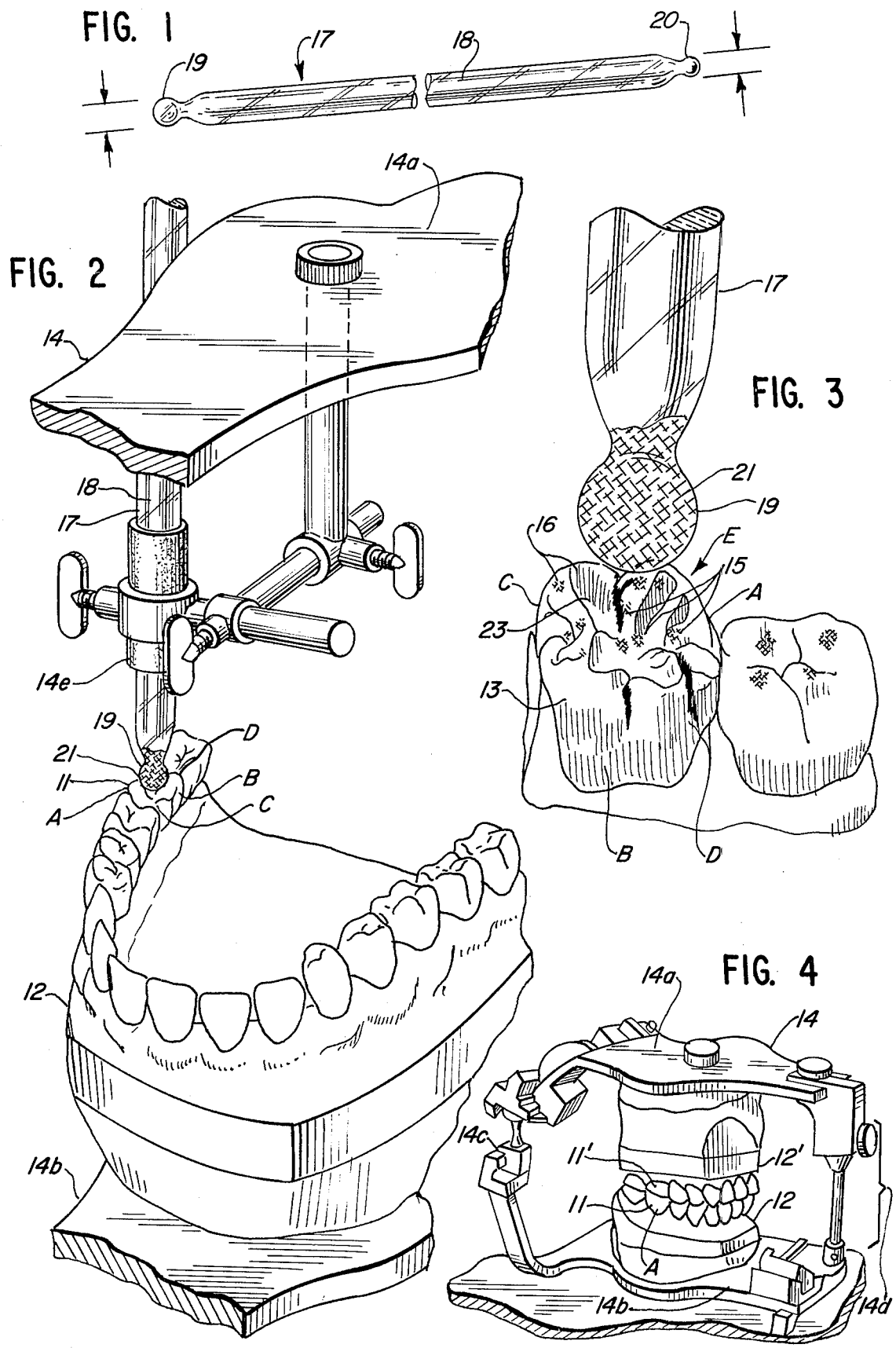

DENTAL METHOD FOR FABRICATING RESTORATIONS

BACKGROUND OF THE INVENTION

Conventionally when a pair of opposing dental restoratives, such as bridges or crowns, or patterns therefor, such as wax patterns, are made, the upper and lower restoratives or patterns are shaped simultaneously with no predetermination of the location of contact points on their occlusal surfaces. The occlusal contact relationship between the restoratives or patterns is determined by trial and error by repeatedly adjusting the occlusal surfaces of both the upper and lower restoratives or patterns until a reasonably acceptable occlusion is obtained therebetween. This approach is very involved and time consuming and often results in restoratives or patterns having imperfect contact points. It is highly desirable to develop simpler and quicker methodology and enabling instrumentation based on standardized guidelines to fabricate opposing restoratives or patterns therefor which have a predetermined standard occlusal contact relationship therebetween. Such methodology and instrumentation would also be beneficial for the purpose of instructing students of dental technology.

SUMMARY OF THE INVENTION

It is therefore a general object of the present invention to provide an improved method and instrument which overcomes the aforesaid problems of the prior art and achieves the aforementioned desirable results.

More particularly, it is an object of the present invention to provide a dental method and instrument for simply and quickly fabricating the first restorative of a pair of opposing restoratives or a pattern therefor based on standardized guidelines.

Similarly, it is an object to provide a standardized dental method and instrument for fabricating a first dental restorative and pattern therefor having a predetermined standard occlusal contact relationship with an opposing second dental restorative.

Other objects and advantages of the invention will become apparent upon reading the following detailed description and appended claims, and upon reference to the accompanying drawings.

These objects are achieved by use of the instrument of this invention. This instrument is adapted for use in fabricating a first dental restorative, or a first pattern therefor having a predetermined standard occlusal contact relationship within an opposing second dental restorative or an opposing second pattern therefor in which the first restorative, or first pattern, have predetermined cusps and fossae. The instrument is used to determine points on the predetermined fossae for potential contact with the second restorative, or second pattern therefor, and each point on the predetermined cusps of potential interference to the predetermined standard occlusal contact relationship with the second restorative, or second pattern. The instrument comprises an elongated handle having an end portion so shaped that a surface thereon simulates the predetermined standard occlusal contact relationship. When this end portion is brought into occlusion with the predetermined fossae, the contact points therebetween represent the predetermined standard occlusal contact points thereon. When the end portion is brought into occlusion with the fossae of the occlusal surface and moved relative thereto so as to simulate the relative lateral and forward motion which might occur beteen the first and second restoratives in a patient's jaws, any point of contact between the end portion and the predetermined cusps indicates a potential interference to the predetermined standard occlusal contact relationship.

In the method of this invention, material (e.g. porcelein paste) which can readily be contoured into a tooth-like shape is applied and shaped on a base or understructure so as to simulate the desired size and configuration of the bucal, lingual, medial and distal surfaces of the first restorative, or the first pattern. The occlusal surface of the first restorative, or the first pattern, is then contoured so as to form the predetermined fossae and cusps. Once the predetermined fossae and cusps have been formed, the end portion of the improved instrument is brought into occlusion with the first restorative or first pattern occlusal surface and moved relative thereto so as to simulate the relative lateral and forward movement which would normally occur between the first and second restoratives when mounted on the patient's jaws. Every point where the predetermined cusps and the end portion of the instrument come into contact will indicate a interference point which will subsequently be removed. Every point where the end portion of the instrument and the predetermined fossae of the first restorative or pattern come into contact, will simulate the standard occlusal contact points on the fossae. All contact points on the fossae in excess of a desired number are subsequently eliminated. Thereafter the occlusal surface of the second restorative, or second pattern, is contoured so as to have the proper biting contact with the first restorative or first pattern. The contact or interference points occasioned by the end portion of this improved instrument will be indicated by a suitable indicating material which is carried on the surface of the instrument end portion and transferred on contact to the surface of the restorative or pattern.

DESCRIPTION

For a more complete understanding of this invention reference should now be made to the embodiment illustrated in greater detail in the accompanying drawings. In the drawings:

FIG. 1 is a fragmentary perspective view of one embodiment of the dental instrument of this invention.

FIG. 2 is a fragmentary perspective view of the instrument of FIG. 1 having one end portion thereof coated with a dye or similar material and showing the instrument mounted on an articulating device and in a occluding relationship with a dental restorative carried by a jaw model mounted on the articulating device.

FIG. 3 is an enlarged fragmentary perspective view of the instrument end portion and the restorative surface of FIG. 2 and showing the restorative occlusal surface subsequent to the instrument end portion being disengaged therefrom and with the contact points on the fossae and the interference points on the cusps being marked by previously transferred portions of the coating on the instrument end portion.

FIG. 4 is a fragmentary perspective view on reduced scale of models of the upper and lower jaws provided with corresponding occluding dental restorations; said jaw model being shown in occluding relation and accommodated in an articulating device.

The fabrication of a pair of dental restoratives, e.g., a pair of crowns 11 and 11[1], normally involves the use of models 12 and 12[1] made from impressions taken of the opposing portions of the patient's jaws where the restoratives are to be placed. The impressions, not shown, from which the models 12 and 12[1] are made may be of either the whole or a portion of the patient's jaws and such impressions are taken after the natural teeth to be crowned have been shaped by grinding or the like so that the base or understructure comprising integral parts of the crowns 11 and 11[1] can be subsequently anchored thereto. Thus the models 12 and 12[1], which are formed of plastic or the like, precisely simulate the sections of the natural jaws in which the crowns 11 and 11[1] are to be located.

Each crown 11 and 11[1] normally includes a porcelain body 13 and 13[1] which is affixed to and projects from the understructure (not shown). The understructure or base is usually formed of metal and serves as a support for the porcelain paste built up thereon during fabrication of the crowns 11 and 11[1] and provides strength to the resulting crowns 11 and 11[1].

Each understructure is placed on the supporting surface of the model of the tooth which is to receive the crown. The understructure is then shaped so as to conform to the contour of the tooth surface. Porcelain paste is then built up and shaped on the understructure. The buildup and formation of the porcelain paste are done by the manual manipulation of one or more tools. During the buildup and formation of the crown the jaw model is mounted on an articulating device 14 which is capable of duplicating various movements and/or relations which occur with the patient's natural jaws. The type of articulating device 14 may vary from that shown without departing from the scope of the claimed invention. In general, the models 12 and 12[1] are secured to separate plate-like members 14a and 14b which are interconnected to each other by an adjustable hinge assembly 14c. The side of each member opposite from the hinge assembly 14c is engaged by an adjustable clamp unit 14d. Both the hinge assembly 14c and the clamp unit 14d permit the members 14a and 14b to be adjusted relative to one another so that the models 12 and 12[1] can simulate certain lateral and forward jaw movements and/or relations (e.g., centric occlusion, lateral excursion and protrusive excursion).

The bucal A, lingual B, medial C and distal D surfaces of the crown 11 and the corresponding surfaces of the crown 11[1] are formed first. In the method of this invention for fabricating opposing crowns 11 and 11[1], contouring of the occlusal surface (not shown) of the crown 11[1] is delayed until after the occlusal surface E of the crown 11 is completely contoured. It is immaterial which crown's occlusal surface is contoured first.

Predetermined standard shaped fossae 15 and cusps 16 are formed in the first occlusal surface E to be contoured. Numerous guidelines can be used for this purpose, and the dental technologist is free to draw on his own experience or the experience of others in contouring the fossae 15 and cusps 16 of the first occlusal surface E. Any imperfections in the predetermined standard fossae 15 and cusps 16 are detected using the standardizing instrument 17 of this invention.

One form of this instrument is shown in FIGS. 1–3 and comprises a rod-like handle 18 which tapers at one end to a first substantially spherical tip 19. The spherical surface of the tip 19, when positioned on the surface E, will make contact points on the surface E which correspond to the predetermined standard occlusal relationship desired between the crowns 11 and 11[1]. Depending upon the size of the opposing crowns 11 and 11[1] and occlusal surface inclination (i.e., inclination from the central fossa to the tip of the bucal cusp or to the tip of the lingual cusp), the tip 19 can have different diameters ranging between 2 mm. and 6 mm. Generally, a series of tips having diameters of 3, 4 and 5 mm. have been found to be suitable for most teeth sizes and occlusal surface inclinations. Thus, the other end of the handle tapers to a second substantially spherical tip 20 having a smaller diameter in the same range. In this way, a plurality of tips can be located on the same instrument.

The tip portions 19 and 20 are shown as integral with the rod-like handle 18 but, if desired, they may be separate pieces which are affixed to the handle by any conventional means. The instrument may be formed of transparent glass or any other suitable hard solid material. The instrument is preferably glass so as not to impede the dental technologist's view of the work area.

In use, a thin transferable coating 21 of a dye or colored material is applied to the exterior of the tip 19 by any convenient manner. The coated tip 19 is then brought into contact with the central fossa region of the occlusal surface E and moved relative thereto so as to simulate the relative lateral and forward movement between the patient's jaws. The articulating device 14 is generally employed to support and position the instrument 17 and the jaw model 12 containing the restorative 11 as shown in FIG. 2 and to produce the relative movement therebetween. A clamp arm 14e is normally used to hold the instrument 17 in proper relative position with respect to the surface region to be contacted thereby. However, an experienced and knowledgeable dental technologist could perform the same operation manually. When contact is made between the tip and the surface E, a portion of the coating 21 will be transferred to the cusps 16 only at the contact points 23. These points represent potential interference to obtaining the desired predetermined standard occlusal contact relationship between the crowns 11 and 11[1]. The contact points may be readily eliminated simply by grinding or scraping the surface of the cusps 16 at the indicated location by means of a suitable tool. The foregoing step is repeated until the desired contouring of the surface has been achieved.

When the tip 19 is brought into contact with the fossae 15 of the occlusal surface E, at substantially the center of the fossa region, as illustrated in FIG. 2, a portion of the tip coating 21 is transferred to the surface of the fossae 15 at only the points 23 of contact between the tip 19 and fossae 15. The colored markings on the fossae indicate potential contact points between the crowns 11 and 11[1].

Since ideal biting contact between occluding teeth is believed to occur only at a limited number of spaced points, all contact points 23 on the fossae 15 in excess of the limited number are eliminated simply by grinding or scraping the surface of the fossae 15 at the excess points 23. Although it is widely regarded in this field that tripodal contact is highly desirable and is preferred, this method permits the dental technologist to use his or her own discretion in selecting the number and location of the desired contact points 23 on the surface of the fossae 15.

It should be noted that both the fossae 15 and cusps 16 can be partially preformed before the instrument 17 is employed. In such case, the interference points 22 on the cusps 16 can be detected before or after the contact points 23 on the fossae 15 are detected. Furthermore, it is possible to form the cusps 16 and detect the interfering contact points 22 thereon before the predetermined fossae 15 are formed. Similarly, it is also possible to form the predetermined fossae 15 and detect the contact points 23 thereon before the predetermined cusps 16 are formed.

For the purpose of determining the standard contact points 23 on the fossae 15 the substantial sphericity of the tip portion 19 is particularly advantageous for it permits the tip 19 to be brought into contact with the fossae 15 from a plurality of angles. This feature minimizes the importance of the angle at which the tip is brought into contact with the fossae 15 and cusps 16. Furthermore, the tip can also be shaped as a hemisphere having a diameter in the range between 2 mm. and 6 mm., or as a cone having a rounded end and a base whose diameter ranges between 2 mm. and 6 mm.

Once the occluding surface E of the restorative 11 has been properly contoured utilizing the instrument 17 as afore-described, the complemental occlusal surface of the other restorative $11^1$ is contoured, using the occlusal surface E of restorative 11 as a standard or guide. Conventional techniques are utilized to form the occluding surface of restorative $11^1$ so that the desired point of occlusal contact between the two crowns 11 and $11^1$ will result. Once the desired occlusal contact has been achieved, the crowns 11 and $11^1$ are removed from the respective teeth of the models 12 and $12^1$, placed in a suitable kiln or oven, and baked until moisture is removed from the porcelain paste and the porcelain bodies 13 and $13^1$ become hardened. Upon the restoratives being removed from the kiln or oven, they are ready to be affixed or anchored to the supporting surface of the natural teeth which had been previously shaped and of which the impression had originally been made.

A variation of the improved method permits the manufacture of gold crowns which, unlike porcelain crowns, do not have separate understructures and are formed from wax patterns. In this case, the same basic procedure is followed except that understructures are not employed and wax instead of porcelain is built up directly on the designated teeth embodied in the models 12 and $12^1$. In this variation, in FIGS. 1-4 the porcelain bodies 13 and $13^1$ would be wax bodies and the crowns 11 and $11^1$ would be wax patterns. After the occlusal surfaces of both wax patterns have been properly contoured so that a predetermined occlusal contact exists between the patterns, a mold is formed about each wax pattern. After the wax patterns are removed from the molds, gold or a similar metal or metal alloy is cast in the molds to form gold crowns which are precise replicas of the wax patterns.

A further variation of this method permits the formation of a single crown which is adapted to have a predetermined standard occlusal contact relationship with an opposing crown which may be added at some time in the future. When one member of a pair of opposing teeth must be crowned, the crown must be contoured to enter into a proper occluding relationship with the opposing natural tooth. Usually no attempt is made to devise an idealized occlusal surface for the crown because it is only necessary that it enter into an occluding relationship with the preexisting non-ideal occlusal surface of the opposing natural tooth. However, it often occurs that after one tooth of a pair of opposing natural teeth is crowned, the other tooth will also be crowned after a short period of time has elapsed. The contour of the new crown is then limited by the fact that improvements were not incorporated into the occlusal surface of the first crown. By anticipating such an occurrence, it is possible to design the occlusal surface of the first crown so that it has standard contact points on the fossae and no interference points on the cusps and thus attains a predetermined standard occlusal contact relationship with a future opposing crown, while at the same time permitting proper occluding to occur with the opposing natural tooth. The same procedure is followed except that porcelain paste is built up and shaped for only one crown 11 and the porcelain member $13^1$ in the model $12^1$ of the opposing jaw section is a duplicate of the opposing natural tooth. When the opposing natural tooth is crowned, its occlusal surface is contoured to contact the first crown at only the standard contact points thereon.

Thus, the improved method and instrument of this invention permit the occlusal surface of a first restorative or a pattern therefor to be completely contoured quickly and simply, using standarized guidelines and even before fabricating an opposing second restorative, or a pattern therefor, so that the first restorative or pattern therefor will enter into a predetermined and improved occlusal relationship with the second restorative, or pattern therefor.

The method and instrument of this invention are also useful in the fabrication of complete dentures made up of individual teeth, each of which has predetermined standard occlusal contact relationship and can be prefabricated in standard sizes.

For the purpose of this specification and the following claims, the term "restorative" shall be used to mean both a dental restorative and a pattern from which a crown, bridge, etc. can be made.

From the above description it is apparent that the objects of this invention have been achieved. While only certain embodiments have been set forth, alternative embodiments and various modifications will be apparent from the above description to those skilled in the art.

Having described the invention, what is claimed is:

1. A method of fabricating a dental restorative having an attaching section and a tooth-shaped section of hardenable material projecting therefrom, the latter section being provided with a predetermined standard occlusal surface including cusps and fossae, said method comprising:
    (a) forming models of opposing portions of a patient's jaws, one of the jaw portions including a segment for supporting the restorative in a predetermined location;
    (b) positioning the attaching section and the tooth-shaped section on the supporting segment of the one-jaw portion model;
    (c) shaping the attaching section to the contour of the supporting segement engaged thereby;
    (d) contacting a predetermined area of the occlusal surface with a segment of an instrument having a rounded exterior shaped to simulate a predetermined standard occlusal contact relationship, the instrument segment having a hardness substantially at least the same as that of the area of the occlusal surface contacted by the instrument segment;
    (e) moving said instrument to generally simulate movement between said patient's jaws;
    (f) imparting indicia on the portions of said surface area contacted by said instrument segment, said indicia identifying said portions of potential interference with the desired occlusion to be effected with said restorative when said models are in occluding relation; and (g) removing a selected number of said identified potential interference portions from the occlusal surface.

2. The method of claim 1 wherein the tooth-shaped section is formed of hardenable material built up on the attaching section to effect a predetermined projection, the predetermined area of the occlusal surface of the tooth-shaped section being contacted by the instrument segment prior to the tooth-shaped section attaining a predetermined hardness.

3. The method of claim 1 wherein the indicia imparted on portions of the surface area includes color contrasting material transferable on contact from a coating of said material applied to the exterior of the instrument segment.

4. The method of claim 1 wherein the instrument segment contacting the surface portion has a substantially spherical configuration and the surface portion is substantially delimited by cusps and fossae.

5. A method of fabricating a dental restorative having an attaching section and a tooth-shaped section of hardenable material projecting therefrom, the latter section being provided with a predetermined occlusal surface including cusps and fossae, including the use of an instrument having a handle section and tip section projecting from said handle section, said tip section having a hardened rounded exterior adapted to contact a predetermined area of the occlusal surface of a dental restorative, said tip section being provided with means for imparting indicia to portions of the surface area upon being contacted by said tip section, said method comprising:

(a) forming models of opposing portions of a patient's jaws, one of the jaw portions including a segment for supporting the restorative in a predetermined location;

(b) positioning the attaching section and the tooth-shaped section on the supporting segment of the one-jaw portion model;

(c) shaping the attaching section to the contour of the supporting segment engaged thereby;

(d) contacting a predetermined area of the occlusal surface with the tip section of the instrument having the hardened rounded exterior shaped to simulate a predetermined standard occlusal contact relationship;

(e) moving the tip section to generally simulate movement between said patient's jaws;

(f) imparting indicia on portions of said surface area contacted by the tip section, said indicia identifying said portions of potential interference with the desired occlusion to be effected with said restorative when said models are in occluding relation; and (g) removing a selected number of said identified potential interference portions from the occlusal surface.

* * * * *